US011459604B2

(12) United States Patent
Collins et al.

(10) Patent No.: US 11,459,604 B2
(45) Date of Patent: Oct. 4, 2022

(54) SYSTEMS AND METHODS FOR PERFORMING VARIABLE SAMPLE PREPARATION AND ANALYSIS PROCESSES

(71) Applicant: LUMINEX CORPORATION, Austin, TX (US)

(72) Inventors: Charles Collins, Austin, TX (US); Dave Smith, Austin, TX (US); Anthony Salvaggio, Austin, TX (US); Alpar Erdei, Austin, TX (US); Gray Mack, Austin, TX (US)

(73) Assignee: LUMINEX CORPORATION, Austin, TX (US)

( * ) Notice: Subject to any disclaimer, the term of this patent is extended or adjusted under 35 U.S.C. 154(b) by 632 days.

(21) Appl. No.: 16/507,166

(22) Filed: Jul. 10, 2019

(65) Prior Publication Data

US 2020/0017901 A1 Jan. 16, 2020

Related U.S. Application Data

(60) Provisional application No. 62/739,982, filed on Oct. 2, 2018, provisional application No. 62/696,961, filed on Jul. 12, 2018.

(51) Int. Cl.

*C12Q 1/686* (2018.01)
*C12Q 1/6837* (2018.01)
(Continued)

(52) U.S. Cl.

CPC ................ *C12Q 1/686* (2013.01); *B01L 7/52* (2013.01); *C12Q 1/6837* (2013.01); (Continued)

(58) Field of Classification Search

None

See application file for complete search history.

(56) References Cited

U.S. PATENT DOCUMENTS 4,202,037 A 5/1980 Glaser et al.
5,018,219 A 5/1991 Matsuzaki et al.
(Continued)

FOREIGN PATENT DOCUMENTS

CN 101657548 2/2010
CN 106460233 2/2017
(Continued)

OTHER PUBLICATIONS

Alexandre, et al., "Colorimetric silver detection of DNA microarrays," *Anal. Biochem.*, 295:1-8, 2001.
(Continued)

*Primary Examiner* — Brian R Gordon

(74) *Attorney, Agent, or Firm* — Parker Highlander PLLC

(57) ABSTRACT

Apparatus and methods for analyzing samples, including for example, samples containing nucleic acids, antibodies, and/or antigens are described. The apparatus may include a frame having a cartridge receiver, two optical devices, thermal cycler, lysis assembly, hybridization heater, and sample transfer assembly. In use, the apparatus may perform multiple sample preparation and analysis processes within the same disposable cartridge including, for example, performing a PCR assay and immunoassay in the same cartridge.

17 Claims, 8 Drawing Sheets

(51) Int. Cl.

| | |
|---|---|
| ***B01L 7/00*** | (2006.01) |
| ***G01N 35/00*** | (2006.01) |
| ***G01N 35/10*** | (2006.01) |
| ***G01N 21/64*** | (2006.01) |

(52) U.S. Cl.

CPC ..... *G01N 21/645* (2013.01); *G01N 35/00584* (2013.01); *G01N 35/10* (2013.01); *G01N 2035/00178* (2013.01); *G01N 2035/00366* (2013.01)

(56) References Cited

U.S. PATENT DOCUMENTS

| | | | | |
|---|---|---|---|---|
| 5,428,690 | A | 6/1995 | Bacus et al. | |
| 5,538,848 | A | 7/1996 | Livak et al. | |
| 5,599,668 | A | 2/1997 | Stimpson et al. | |
| 5,804,375 | A | 9/1998 | Gelfand et al. | |
| 6,143,247 | A | 11/2000 | Sheppard, Jr. et al. | |
| 6,212,292 | B1 | 4/2001 | Soares | |
| 6,214,560 | B1 | 4/2001 | Yguerabide et al. | |
| 6,248,988 | B1 | 6/2001 | Krantz | |
| 6,268,218 | B1 | 7/2001 | Pantoliano et al. | |
| 6,286,763 | B1 | 9/2001 | Reynolds et al. | |
| 6,396,941 | B1 | 5/2002 | Bacus et al. | |
| 6,506,564 | B1 | 1/2003 | Mirkin et al. | |
| 6,602,669 | B2 | 8/2003 | Letsinger et al. | |
| 6,649,403 | B1 | 11/2003 | McDevitt et al. | |
| 6,728,417 | B1 | 4/2004 | Hara et al. | |
| 6,750,016 | B2 | 6/2004 | Mirkin et al. | |
| 7,163,823 | B2 | 1/2007 | Patno et al. | |
| 7,250,499 | B2 | 7/2007 | Mirkin et al. | |
| 7,321,829 | B2 | 1/2008 | Remacle et al. | |
| 7,396,677 | B2 | 5/2008 | Petrovic et al. | |
| 7,422,850 | B2 | 9/2008 | Marshall et al. | |
| 7,695,952 | B2 | 4/2010 | Patno et al. | |
| 7,727,473 | B2 | 6/2010 | Ching et al. | |
| 7,773,790 | B2 | 8/2010 | Cork et al. | |
| 7,888,107 | B2 | 2/2011 | Patno et al. | |
| 8,372,340 | B2 | 2/2013 | Bird et al. | |
| 8,698,101 | B2 | 4/2014 | Jaffe et al. | |
| 9,115,393 | B2 | 8/2015 | Doebler, II et al. | |
| 9,248,422 | B2 | 2/2016 | Ching et al. | |
| 9,827,567 | B2 | 11/2017 | Westberg et al. | |
| 2001/0012612 | A1* | 8/2001 | Petersen ................ | B01L 3/502<br>435/5 |
| 2002/0177135 | A1* | 11/2002 | Doung ................. | B01L 3/5027<br>435/287.2 |
| 2003/0095764 | A1 | 5/2003 | Pering et al. | |
| 2003/0129094 | A1 | 7/2003 | Schubert et al. | |
| 2003/0224505 | A1 | 12/2003 | Patno et al. | |
| 2004/0014106 | A1 | 1/2004 | Patno et al. | |
| 2006/0013744 | A1 | 1/2006 | Mikkelsen et al. | |
| 2006/0246580 | A1* | 11/2006 | Kim ......................... | B01L 7/52<br>435/303.1 |
| 2008/0063573 | A1* | 3/2008 | Ammann ................. | B01L 7/52<br>422/105 |
| 2008/0305481 | A1 | 12/2008 | Whitman et al. | |
| 2009/0021728 | A1* | 1/2009 | Heinz ................. | C12Q 1/6844<br>356/244 |
| 2009/0074624 | A1 | 3/2009 | Liang | |
| 2009/0139311 | A1* | 6/2009 | Lehto ................. | B01L 3/50851<br>73/864.91 |
| 2009/0191097 | A1 | 7/2009 | Hanafusa et al. | |
| 2009/0221059 | A1* | 9/2009 | Williams ............ | F16K 99/0061<br>422/400 |
| 2009/0298129 | A1 | 12/2009 | Spence et al. | |
| 2010/0136563 | A1* | 6/2010 | Keller ...................... | B01L 7/52<br>435/6.12 |
| 2010/0173394 | A1* | 7/2010 | Colston, Jr. ............. | B01L 7/525<br>422/68.1 |
| 2013/0071946 | A1 | 3/2013 | Burghardt et al. | |
| 2013/0130369 | A1 | 5/2013 | Wilson et al. | |
| 2013/0230860 | A1* | 9/2013 | Park ....................... | B03C 1/288<br>435/6.12 |
| 2013/0288259 | A1 | 10/2013 | Tajima | |
| 2013/0337432 | A1 | 12/2013 | Cook et al. | |
| 2014/0005078 | A1 | 1/2014 | Howell et al. | |
| 2014/0038192 | A1 | 2/2014 | Buse et al. | |
| 2015/0037803 | A1* | 2/2015 | Park .................... | C12Q 1/6804<br>435/6.12 |
| 2015/0298120 | A1 | 10/2015 | Westberg et al. | |
| 2015/0308958 | A1 | 10/2015 | Lemieux et al. | |
| 2015/0346097 | A1* | 12/2015 | Battrell ............. | G01N 21/6428<br>702/19 |
| 2016/0054343 | A1* | 2/2016 | Holmes ............. | G01N 35/0098<br>422/65 |
| 2016/0090588 | A1 | 3/2016 | Lofquist et al. | |
| 2016/0101421 | A1 | 4/2016 | Ching et al. | |
| 2016/0216289 | A1 | 7/2016 | Augstein et al. | |
| 2016/0265040 | A1* | 9/2016 | Baumgartner ....... | G01N 21/645 |
| 2016/0320283 | A1 | 11/2016 | Spriggs | |
| 2017/0003310 | A1* | 1/2017 | Shohmi ............ | G01N 35/00584 |
| 2017/0199210 | A1* | 7/2017 | Ang ................. | G01N 35/00732 |
| 2018/0193831 | A1* | 7/2018 | Hopper ................... | F04B 43/00 |
| 2018/0282788 | A1* | 10/2018 | Opalsky ............ | G01N 35/1009 |
| 2019/0221289 | A1* | 7/2019 | Stahl .................... | H05K 1/0204 |
| 2020/0290037 | A1* | 9/2020 | Salomon ............ | G01N 35/0099 |
| 2020/0292568 | A1* | 9/2020 | Yavets-Chen ...... | G01N 35/1002 |
| 2020/0300877 | A1* | 9/2020 | Choi ................. | G01N 21/6428 |
| 2021/0071242 | A1* | 3/2021 | Tidd ................ | G01N 35/00722 |
| 2022/0008928 | A1* | 1/2022 | Colston, Jr. ......... | B29C 45/0053 |

FOREIGN PATENT DOCUMENTS

| | | |
|---|---|---|
| WO | WO 98/44330 | 10/1998 |
| WO | WO 99/13319 | 3/1999 |
| WO | WO 02/086468 | 10/2002 |
| WO | WO 03/053535 | 7/2003 |
| WO | WO 03/060446 | 7/2003 |
| WO | WO 2015/160863 | 10/2015 |

OTHER PUBLICATIONS

Brown, et al., "Image metrics in the statistical analysis of DNA microarray data," *PNAS*, 98:8944-8949, 2011.

Doseeva, et al, "Multiplex isothermal helicase-dependent amplification assay for detection of Chlamydia trachomatis and Neisseria gonorrhea," *Diagn. Microbiol. Infect. Dis*., 71:354-65, 2011.

Final Search Report and Written Opinion, issued in PCT/US2019/041105, dated Nov. 20, 2019.

Partial Search Report and Invitation to Pay Additional Fees, issued in PCT/US2019/041105, dated Sep. 27, 2019.

Sonnichsen, et al., "Spectroscopy of single metallic nanoparticles using total internal reflection microscopy," *Appl. Phys. Lett*., 77:2949-51, 2000.

Storhoff, et al., "Homogeneous detection of unamplified genomic DNA sequences based on colorimetric scatter of gold nanoparticle probes," *Nat. Biotechnol*., 22:883-7, 2004.

Storhoff, et al., "Gold nanoparticle-based detection of genomic DNA targets on microarrays using a novel optical detection system," *Biosens. Bioelectron*., 19:875-83, 2004.

Takahagi, et al., "Scanning Electron Microscope Observation of Heterogeneous Three-Dimensional Nanoparticle Arrays Using DNA," *Japanese Journal of Applied Physics*, 40:L521, 2001.

Taton, et al., "Scanometric DNA array detection with nanoparticle probes," *Science*, 289:1757-60, 2000.

Office Action issued in Chinese Patent Application No. 201980046842.1, dated May 26, 2022.

* cited by examiner

SYSTEMS AND METHODS FOR PERFORMING VARIABLE SAMPLE PREPARATION AND ANALYSIS PROCESSES

CROSS-REFERENCE TO RELATED APPLICATIONS

The present application claims the priority benefit of U.S. provisional patent application, Ser. No. 62/696,961, filed Jul. 12, 2018, and U.S. provisional patent application, Ser. No. 62/739,982, filed Oct. 2, 2018, the entire contents of which is incorporated herein by reference.

FIELD OF THE INVENTION

Embodiments of the present invention relate generally to the fields of life science research and in vitro diagnostics. More particularly, embodiments of the present invention relate to apparatus, systems, and methods for analyzing samples, including for example, samples containing nucleic acids, antibodies, and/or antigens.

BACKGROUND

Biological samples are analyzed for a variety of research, monitoring, or diagnostic purposes. Typically, a particular sample, or a portion of that sample, is analyzed for the presence of either a target nucleic acid sequence, a target antibody, or a target antigen. Where the target is a nucleic acid sequence, the process typically includes isolating nucleic acids within a sample through a series of several steps, such as: (1) lysing cells in the sample to expose nucleic acids contained therein, (2) denaturing and/or degrading proteins in the sample using detergents and/or enzymes (e.g., Proteinase K); (3) precipitating the nucleic acid from the sample; and (4) washing and/or otherwise preparing the nucleic acid for further analysis. The isolated nucleic acid may then be amplified if desired for further analysis. The polymerase chain reaction (PCR) process is a known technique for amplifying portions of a nucleic acid molecule. During a PCR, an input sample containing the target DNA is mixed with reagents, which include the DNA polymerase (e.g., Taq polymerase). The input sample can be, for example, the isolated nucleic acid sample produced by the procedure described above. The sample is then thermally cycled multiple times within a chamber to complete the reaction. After the DNA sequence is sufficiently amplified, it can be analyzed using various optical techniques. Sample processing for nucleic acid isolation and amplification as described above is not compatible with immunoassays because the various reagents and temperatures employed will destroy the proteins in the sample. Accordingly, a different approach that preserves binding epitopes of the target proteins is used when preparing samples for an immunoassay.

There are some known systems for substantially automating the sample analysis process, but these systems are generally capable of only analyzing nucleic acids or only analyzing proteins. Additionally, these systems are generally only capable of analyzing a particular sample quantitatively or qualitatively. Accordingly, users have to run multiple tests on multiple different instruments in order to obtain, for example, both a nucleic acid test result and an immunoassay test result on a particular sample. Or, as a further example, a user may have to divide the sample for multiple tests on the same or different instruments in order to examine multiple nucleic acid target sequences, particularly where the user is interested in obtaining quantitative results for a subset of those target sequences.

Thus, a need exists for systems and methods for processing and analyzing samples for different testing needs. While not limiting the scope of the present disclosure, various embodiments of the present invention address issues of existing systems, including efficiency and flexibility factors as noted above.

SUMMARY OF THE INVENTION

Exemplary embodiments of the present disclosure relate to methods, devices and systems for sample processing and analysis by, for example polymerase chain reaction (PCR) and/or immunoassay. Various embodiments provide improved workflow and flexibility by combining sample preparation and analysis in a single cartridge, including the ability to accommodate multiple sample preparation and analysis processes within the same cartridge if needed (e.g., real-time PCR and immunoassay in the same cartridge or real-time PCR and endpoint PCR in the same cartridge). Moreover, various embodiments provide housings that can accommodate multiple frames configured to perform assays in disposable cartridges, including accommodating frames equipped with different components. This modular configuration offers several advantages. First, a user need only purchase the number of frames needed to meet his or her test volume requirements. Second, if one frame needs repaired it can quickly be removed for repair (with a replacement frame optionally swapped in at the same time) with no instrument downtime. In addition, the modular configuration enables the accommodation of different frame configurations within the same housing, which provides flexibility in terms of the types of assays that can be run in one housing. It also allow users to later add an additional frame to meet increased volume, a different frame for new assay needs, or upgrade to a newer frame without needing to replace an entire system.

One embodiment provides an apparatus, comprising: an enclosure configured to receive a cartridge that includes a biological sample; a first optical device configured to perform a first optical analysis of a first assay performed in a first region of the cartridge when the cartridge is disposed in the enclosure; a second optical device configured to perform a second optical analysis of a second assay performed in a second region of the cartridge when the cartridge is disposed in the enclosure, wherein the second assay is a different type of assay than the first assay. In certain embodiments, the apparatus further comprises an interface circuit configured to receive electronic instructions to use the first optical device to perform the first optical analysis on a first subset of the biological sample, and/or to use the second optical device to perform a second optical analysis on a second subset of the biological sample.

The cartridge may be, for example, a cartridge as shown in FIG. 2 or a cartridge as described in U.S. Pat. No. 9,827,567, which is incorporated herein by reference. The enclosure at least partially supports the cartridge when the cartridge is disposed within the apparatus. In certain embodiments, the enclosure is configured to move relative to other components of the apparatus in order to, for example, facilitate the insertion of the cartridge into the apparatus, facilitate the ejection of the cartridge from the apparatus, place the cartridge in optical communication with an optical device of the apparatus (e.g., the first optical device or the second optical device), and/or place the cartridge in thermal communication with a heating/cooling device of the apparatus (e.g., a thermal cycler, lysis assembly heater, hybridization heater).

The first optical device may be any device capable of emitting and receiving electromagnetic radiation suitable for use in the first assay. The first optical device may, for example, comprise one or more electromagnetic radiation emitters such as lasers, light emitting diodes (LEDs), or incandescent bulbs. The first optical device may, for example, comprise one or more electromagnetic radiation detectors such as a charge coupled device (CCD), complementary metal-oxide semiconductor (CMOS), photomultiplier tube, avalanche photodiode, or silicone photodiode. In some embodiments, the electromagnetic radiation that is emitted and/or received by the first optical device has a wavelength between about 300 nm and 900 nm.

The biological sample may be any sample that contains or is suspected of containing biological components such as nucleic acids (e.g., DNA or RNA), proteins (e.g., antibodies or antigens), lipids, or carbohydrates. In certain embodiments, the sample may be, for example, a clinical or research sample obtained from or contrived from a human, animal, plant, or microorganism. In other embodiments, the sample may be, for example, an environmental sample such as a water, soil, food, or air sample.

In certain embodiments, the first region of the cartridge is an amplification region and the first assay is a nucleic acid amplification assay. The amplification region may be an amplification region such as that indicated in FIG. 4B. Where the first assay is a nucleic acid amplification assay, the biological sample will be a sample that contains or is suspected of containing a nucleic acid. The nucleic acid amplification assay may be, for example, a polymerase chain reaction (PCR) assay or an isothermal amplification reaction. In some embodiments, the PCR assay is a real-time PCR assay. Various real-time PCR chemistries may be used including, for example, chemistries as described in U.S. Pat. Nos. 5,538,848, 5,804,375, and 7,422,850, each of which is incorporated herein by reference.

The apparatus may further comprise a thermal cycler assembly configured to engage an amplification tube assembly in the amplification region of the cartridge such that thermal cycler assembly can raise, lower, and/or hold substantially constant the temperature of the contents of amplification tube assembly according to a desired protocol for the nucleic acid amplification (e.g., PCR, isothermal amplification). The apparatus may further comprise an interface circuit configured to receive electronic instructions to raise, lower, or maintain the temperature of the thermal cycler. In certain embodiments, the thermal cycler assembly comprises an amplification tube block having an internal shape that fits amplification tube assembly such that there is consistent contact between the inner surfaces of the amplification tube block and outer surfaces of the amplification tube(s). In addition, in certain embodiments, the amplification tube block will have one or more openings configured to allow optical communication between the amplification tube(s) and the first optical device. In some embodiments, one or more optical fibers are disposed in the one or more openings in the amplification tube and transmit electromagnetic radiation to and from the first optical device and the amplification tube or tubes. In particular embodiments, the first optical device comprises: a fluorimeter; and a plurality of optical cables configured to transmit light between the fluorimeter and the first region of the cartridge when the cartridge is disposed in the enclosure.

In order to raise, lower, and/or hold substantially constant the temperature of the nucleic acid amplification assay, the thermal cycler assembly includes a heating/cooling element. The heating/cooling element may be, for example, a peltier cell or thermoelectric couple (TEC). The thermal cycler assembly may further comprise (i) a heat sink to facilitate the transfer of heat away from the thermal cycler assembly, (ii) one or more thermistors to profile the temperature of the amplification tube block, and/or (iii) an amplification processor to facilitate electrical connection of the heating/cooling element and/or the thermistors to a frame interface circuit and/or a system control circuit.

In certain embodiments, the second imaging region of the cartridge is a hybridization imaging region. In some embodiments, the hybridization imaging region comprises a substantially planar surface upon which analytes may be positioned for imaging by the second imaging device of the apparatus. Analytes may be positioned in the hybridization imaging region using, for example, a spotted array or beads. For example, a target DNA, RNA, antibody, or antigen may be directly or indirectly hybridized to a spotted probe array within the hybridization imaging region, and the hybridization event detected using the second optical device of the apparatus. The detection may be facilitated through the use of labels, such as fluorophores or metals. Multiple different targets may be detected simultaneously based on their x and y coordinates within the hybridization imaging region. As another example, a target DNA, RNA, antibody, or antigen may be directly or indirectly hybridized to a bead within the hybridization imaging region, and the hybridization event detected using the second optical device of the apparatus. Multiple different targets may be detected simultaneously, by for example, using a plurality of encoded beads.

The second optical device may be any device capable of emitting and receiving electromagnetic radiation suitable for use with the labeling scheme in the second assay. The second optical device may, for example, comprise one or more electromagnetic radiation emitters such as lasers, light emitting diodes (LEDs), or incandescent bulbs. The second optical device may, for example, comprise one or more electromagnetic radiation detectors such as a charge coupled device (CCD), complementary metal-oxide semiconductor (CMOS), photomultiplier tube, avalanche photodiode, or silicone photodiode. In some embodiments, the electromagnetic radiation that is emitted and/or received by the second optical device has a wavelength between about 300 nm and 900 nm. The detector senses electromagnetic radiation, converts the sensed electromagnetic radiation into a data format and sends the data to processor. In certain embodiments, the detector senses light in the visible light spectrum, the infrared light bands, and/or the ultraviolet bands. The electromagnetic radiation emitter illuminates all or a portion of the hybridization imaging surface with electromagnetic radiation. The electromagnetic radiation may be in the visible light spectrum, the infrared light bands, and/or the ultraviolet bands, although other wavelengths may be used. Further, the electromagnetic radiation emitter may generate a specific wavelength of light or a spectrum of wavelengths, such as white light. A variety of electromagnetic radiation emitter configurations may be used, such as side-lighting, front-lighting, and backlighting. Polarizers and filters can also be used to modify the incident light. When side-lighting, the electromagnetic radiation emitter may couple to at least one side of the hybridization imaging surface so as to utilize the waveguiding capabilities of glass or another suitable substrate that forms the hybridization imaging surface. Coupling of the electromagnetic radiation emitter to the hybridization imaging surface may be accomplished in a variety of ways such as by a fiber optic bundle, a solid waveguide, and or a laser beam or LEDs glancing along the substrate. In a particular embodiment the electromagnetic radiation emitter is positioned to side-light or front-light the hybridization imaging surface and the detector is position above or below the hybridization imaging surface such that the detector detects scattered light from the sample, such as scattered light from metallic nanoparticles used to label target analytes in the sample, on the hybridization imaging surface. In another embodiment the electromagnetic radiation emitter is positioned to illuminate the hybridization imaging surface at a first wavelength and the detector is position to detect electromagnetic radiation emitted from the hybridization imaging surface at a second wavelength, such as the emission wavelength of a fluorescent dye used to label target analytes in the sample on the hybridization imaging surface and/or the emission wavelength of a fluorescent dye used to label microspheres on the hybridization imaging surface.

The apparatus may also include one or more magnets configured to exert a magnetic force on certain locations in the cartridge. In one embodiment, the apparatus comprises a magnet assembly configured to exert magnetic force on the second imaging region. The magnetic force can be applied or removed from the hybridization imaging surface by, for example, moving the magnet and the second imaging region relative to each other, by placing or removing a shield material between the magnet and the second imaging region, or by employing an electromagnet that can be turned on and off. The magnet may be used with, for example, with magnetically responsive, fluorescently encoded microspheres in the second imaging region. The magnetic field may be used to immobilize the fluorescently encoded microspheres on the surface of the second imaging region to facilitate their detection.

Additionally, the apparatus may further comprise any combination of one or more of the following: a lysis assembly, a hybridization heater, a sample transfer assembly, a lift motor, a cartridge receiver, and/or a barcode reader.

The lysis assembly is configured to engage the sample preparation region of the cartridge. In certain embodiments, the lysis assembly may comprise any combination of one or more of (i) a lysis heater configured to transfer heat the sample preparation region or a portion thereof, (ii) a magnet configured to be selectively engaged with the sample preparation region or a portion thereof, such that when the magnet is engaged magnetically responsive particles in the sample preparation region of the cartridge can be immobilized in a desired location within sample preparation region; (iii) a sonication horn configured to provide acoustic energy to the contents of the sample preparation region or a portion thereof; and/or (iv) a processor to facilitate electrical connection of the lysis heater and/or the magnet and/or the sonication horn to an interface circuit and/or a system control circuit.

The hybridization heater is configured to engage various features in the hybridization region of a cartridge when a cartridge is present in the apparatus. In certain embodiments, the hybridization heater may comprise one or more of the following: (i) a heating/cooling element, such as a peltier cell or thermoelectric couple (TEC); (ii) a heat sink; (iii) one or more thermistors; and/or (iv) a processor to facilitate electrical connection of the heating/cooling element and/or the thermistors to an interface circuit and/or a system control circuit.

The sample transfer assembly is configured to transfer the biological sample within a cartridge when a cartridge is disposed in the apparatus. In one embodiment, the cartridge comprises one or more pipette tips and the sample transfer assembly is configured to selectively engage the one or more pipette tips when cartridge is disposed within the apparatus. In such an embodiment, the sample transfer assembly comprises one or more transfer heads, which fit the one or more pipette tips. In certain embodiments, the sample transfer assembly may comprise a tip pusher configured to disengage the transfer head from the pipette tip at the desired time. In some embodiments, the sample transfer assembly comprises a pressure regulating device, such as a pump, to permit fluid to be drawn into or ejected out of a pipette tip when engaged with the transfer head of the sample transfer device. In certain embodiments, the sample transfer assembly comprises a device for moving the transfer head in one or more of the x, y, and z axis. For example, this may include an x-rail, a y-rail, and a z-rail, along which the transfer head travels under the power of an x-motor, a y-motor, and a z-motor.

The lift motor is configured to provide relative movement between the cartridge and one or more components of the apparatus in order to facilitate insertion and/or removal of the cartridge. In one embodiment, for example, the lift motor is configured to raise and lower the optical device in order to facilitate the insertion of the cartridge into the apparatus and/or facilitate the optical communication between the optical device and the hybridization imaging region. In another embodiment, for example, the lift motor is configured to raise and lower a cartridge receiver in order to facilitate the insertion of cartridge into the cartridge receiver and/or facilitate an interaction between the cartridge and one or more components of the apparatus, including interaction with one or more of the first optical device, second optical device, thermal cycler, lysis assembly, hybridization heater, sample transfer assembly, and/or a barcode reader.

In certain embodiments, the apparatus may further comprise a frame, which may also be referred to as a biological assay frame. The frame contains the components of the apparatus in any of the various configurations disclosed herein and structurally supports these components either directly or indirectly. In some embodiments, the frame is configured to be removably disposed in a housing configured to accommodate one frame or a plurality of frames.

In one embodiment, a system is provided, comprising: (a) an instrument housing comprising a plurality of instrument bays, each of which is configured to hold a corresponding biological assay frame, which frame may comprise any apparatus configuration disclosed herein; (b) a biological assay control circuit configured to: (i) receive, via a user interface, a request to perform a biological assay on at least one sample inserted into a particular biological assay frame within the instrument housing; (ii) instruct the particular biological assay frame to perform the request to perform the biological assay; and (iii) output, via the user interface based on information received from the biological assay frame, results of the biological assay; (c) a plurality of electrical connectors configured to connect the biological assay control circuit to biological assay frames held within each of the plurality of instrument bays.

In certain embodiments, the system further comprises (a) a first biological assay frame disposed within a first instrument bay of the plurality of instrument bays; (b) a second biological assay frame disposed within a second instrument bay of the plurality of instrument bays; and (c) a third biological assay frame disposed within a third instrument bay of the plurality of instrument bays. In some embodiments, each of the first, second, and third biological assay frames comprises: an enclosure configured to receive a cartridge that includes a biological sample; a first optical device configured to perform a first optical assay on a first region of the cartridge when the cartridge is disposed in the enclosure; a second optical device configured to perform a second optical assay on a second region of the cartridge when the cartridge is disposed in the enclosure, wherein the second optical assay is a different type of optical assay than the first optical assay; and an interface circuit configured to receive electronic instructions to use the first optical device to perform the first optical assay on a first subset of the biological sample, and to use the second optical device to perform a second optical assay on a second subset of the biological sample. In particular embodiments, at least one of the first, second, and third biological assay frames comprises: an enclosure configured to receive a cartridge that includes a biological sample; a first optical device configured to perform a first optical assay on a first region of the cartridge when the cartridge is disposed in the enclosure; a second optical device configured to perform a second optical assay on a second region of the cartridge when the cartridge is disposed in the enclosure, wherein the second optical assay is a different type of optical assay than the first optical assay; and an interface circuit configured to receive electronic instructions to use the first optical device to perform the first optical assay on a first subset of the biological sample, and to use the second optical device to perform a second optical assay on a second subset of the biological sample. In particular embodiments, at least one of the first, second, and third biological assay frames comprises: the enclosure configured to receive the cartridge that includes a biological sample; the second optical device configured to perform the second optical assay on the second region of the cartridge when the cartridge is disposed in the enclosure; and an interface circuit configured to receive electronic instructions to use the second optical device to perform an optical assay on the biological sample in the second region of the cartridge; wherein the at least one of the first, second, and third biological assay frames does not have the first optical device configured to perform the first optical assay on the first region of the cartridge when the cartridge is disposed in the enclosure.

The present invention also provides various methods for performing assays, including assays performed in a system or apparatus as described herein. In one embodiment, a method is provided for performing a multiplex biological assay comprising: inserting a cartridge that includes a biological sample into an apparatus comprising a first optical device and a second optical device; using the first optical device to perform a first optical assay on the biological sample in the first region of the cartridge; and using the second optical device to perform a second optical assay on the biological sample, wherein the second optical assay is different from the first optical assay.

In another embodiment, a method is provided for performing a multiplex biological assay, the method comprising: inserting a cartridge that includes a biological sample comprising nucleic acids into an apparatus comprising a first optical device, a second optical device, a sample transfer device, and a thermal cycler; using the sample transfer device of the apparatus to transfer the biological sample from a sample well of the cartridge to a first region of the cartridge; using the thermal cycler to perform a polymerase chain reaction on a plurality of target nucleic acid sequences; using the first optical device to assay the polymerase chain reaction in real time for a first subset of the target nucleic acid sequences; using the sample transfer device of the apparatus to transfer the biological sample from the first region to a second region of the cartridge; and using the second optical device to perform end-point analysis of the polymerase chain reaction for a second subset of the target nucleic acid sequences. In certain embodiments, the first subset of the target nucleic acid sequences comprises 1, 2, 3, 4, 5, 6, 7, 8, 9, 10, 11, 12, 13, 14, 15, or 16, or any range derivable therein, target nucleic acid sequences. In certain embodiments, the second subset of the target nucleic acid sequences comprises from 1 to 100, 1 to 50, 1 to 30, 5 to 50, 5 to 30, or 12 to 30 target nucleic acid sequences. In one embodiment, the first subset of the target nucleic acid sequences comprises 1 to 6 target nucleic acid sequences, and the second subset of the target nucleic acid sequences comprises 5 or more target nucleic acid sequences. In some embodiments, the method further comprises quantitating the amount of target nucleic acid sequences in the first subset of the target nucleic acid sequences. The method may, in some embodiments, further comprise using the sample transfer device to transfer the biological sample to one or more sample extraction wells of the cartridge prior to transferring the biological sample to the first region of the cartridge. Additionally or alternatively, the method may, in some embodiments, further comprise using the sample transfer device to transfer the biological sample to one or more hybridization wells of the cartridge prior to transferring the biological sample to the second region of the cartridge.

In another embodiment, a method is provided for performing a multiplex biological assay, the method comprising: (a) inserting a cartridge that includes a biological sample comprising proteins and nucleic acids into an apparatus comprising an enclosure configured to receive the cartridge, a sample transfer device, a thermal cycler, a first optical device, and a second optical device; (b) using the sample transfer device of the apparatus to transfer a first subset of the biological sample from a sample well of the cartridge to a first region of the cartridge; (c) using the sample transfer device of the apparatus to transfer a second subset of the biological sample from the sample well of the cartridge to a second region of the cartridge; (d) using the thermal cycler and a first optical device to perform a polymerase chain reaction on the first subset of the biological sample; and (e) using the second optical device to perform an immunoassay on the second subset of the biological sample in the second region of the cartridge.

In some embodiments, the apparatus in which a method is performed is one of a plurality of apparatuses removably disposed within an instrument housing, the instrument housing further comprising: (a) a biological assay control circuit configured to: (i) receive, via a user interface, a request to perform a biological assay on at least one sample inserted into a particular apparatus of the plurality of apparatuses disposed within the instrument housing; (ii) instruct the particular apparatus to perform the request to perform a biological assay or assays; and (iii) output, via the user interface based on information received from the particular apparatus, results of the biological assay; and (b) a plurality of electrical connectors configured to connect the biological assay control circuit to the plurality of apparatuses disposed within the instrument housing.

In another embodiment, a method is provided for performing a biological assay, the method comprising: (a) inserting a cartridge that contains a biological sample into an apparatus, wherein the cartridge comprises: (i) a sample well containing the biological sample; (ii) at least amplification tube; (iii) at least one hybridization tube; (iv) a hybridization imaging assembly; and (v) at least one pipette tip movable in an x, y, and z-axis; and wherein the apparatus comprises:

(i) an enclosure configured to receive a cartridge that includes a biological sample; (ii) a sample transfer assembly configured to transfer the biological sample within the cartridge; (iii) a thermal cycler configured to receive a first region of the cartridge when the cartridge is disposed within the enclosure; (iv) a first optical device configured to perform a first optical assay on the first region of the cartridge when the cartridge is disposed in the enclosure; (v) a second optical device configured to perform a second optical assay on a second region of the cartridge when the cartridge is disposed in the enclosure, wherein the second optical assay is a different type of optical assay than the first optical assay; and (vi) an interface circuit configured to receive electronic instructions to: use the sample transfer assembly to transfer the biological sample within the cartridge; raise, lower, or maintain the temperature of the thermal cycler; use the first optical device to perform the first optical assay on the biological sample or a first subset of the biological sample; and use the second optical device to perform the second optical assay on the biological sample or a first subset of the biological sample; (b) transferring, using the sample transfer assembly and the pipette tip, at least a portion of the biological sample from the sample well to the amplification tube; (c) transferring, at least a portion of the biological sample from the amplification tube to the hybridization tube; and (d) transferring, using the sample transfer assembly and the pipette tip, the biological sample from the hybridization tube to the hybridization imaging assembly. In some embodiments, the method further comprises: (a) performing, using the first optical device, a first assay on the biological sample or a first subset of the biological sample in the amplification tube; and/or (b) performing, using the second optical device, a second assay on the biological sample or a second subset of the biological sample in the hybridization imaging assembly. In some embodiments, the method further comprises: (a) a first portion of the biological sample is transferred, using the sample transfer assembly and the pipette tip, to a lysis well; (b) a second portion of the biological sample is transferred, using the sample transfer assembly and the pipette tip, to a hybridization tube; (c) the first portion of the biological sample is transferred, using the sample transfer assembly and the pipette tip, from the lysis well to the amplification tube; and (d) the second portion of the biological sample is transferred, using the sample transfer assembly and the pipette tip, from the hybridization tube to the hybridization imaging assembly.

In certain embodiments, the biological sample is transferred, using the sample transfer assembly and the pipette tip, to a lysis well prior to transferring the biological sample to the amplification tube. The biological sample may be combined with a lysis reagent in the lysis well. The lysis reagent may comprise, for example, one or more of the following: a detergent (e.g., Triton X, SDS), a chaotropic agent, a salt (e.g., Tris-HCl, EDTA), dithiothreitol (DTT), and/or an enzyme (e.g., protease).

In certain embodiments, the method further comprises performing, using the first optical device, an assay on the biological sample or a first subset of the biological sample in the amplification tube. The assay may be, for example, PCR or another nucleic acid amplification technique. The assay may be configured to amplify one target nucleic acid sequences or a plurality of different target nucleic acid sequences if the target nucleic acid sequences are present in the biological sample. In certain embodiments, the assay is configured to amplify from 2 to 50 different target nucleic acid sequences if the target nucleic acid sequences are present in the biological sample.

In some embodiments, amplification of a first subset of the target nucleic acid sequences is assayed by real-time PCR in the amplification tube, and amplification of a second subset of the target nucleic acid sequences is assayed, using the second optical device, by a probe hybridization assay in the hybridization imaging assembly.

In certain embodiments, the first portion of the biological sample is assayed, using the first optical device, by PCR or other nucleic acid amplification technique in the amplification tube; and the second portion of the biological sample is assayed, using the second optical device, by an immunoassay in the hybridization imaging assembly.

Particular embodiments include an optical device comprising: (a) a first housing having an interior and an exterior; (b) a plurality of light sources disposed within the interior of the first housing; (c) for each light source of the plurality of light sources at least one mirror disposed within the interior of the first housing and configured to direct at least a portion of light emitted from each light source along a common path through at least one port extending from the interior of the first housing to the exterior of the first housing; (d) a second housing having an interior and an exterior; (e) a port extending from the exterior of the second housing to the interior of the second housing; (f) a plurality of detectors disposed within the interior of the second housing; and (g) a plurality of mirrors disposed within the interior of the second housing and in a path of light entering the interior of the second housing through the port extending from the exterior of the second housing to the interior of the second housing, where the plurality of mirrors are configured to direct at least a portion of light entering the interior of the second housing through the port extending from the exterior of the second housing to the interior of the second housing to the plurality of detectors.

Certain embodiments include an optical device comprising: (a) a first housing having an interior and an exterior; (b) five light sources disposed within the interior of the first housing; (c) for each of the five light sources at least one mirror disposed within the interior of the first housing and configured to direct at least a portion of light emitted from each of the five light sources along a common path through four ports extending from the interior of the first housing to the exterior of the first housing; (d) a second housing having an interior and an exterior; (e) four ports extending from the exterior of the second housing to the interior of the second housing; (f) an array of twenty detectors disposed within the interior of the second housing; and (g) at least five mirrors disposed within the interior of the second housing and in a path of light entering the interior of the second housing through each of the four ports extending from the exterior of the second housing to the interior of the second housing, where the five mirrors are configured to direct at least a portion of light entering the interior of the second housing through the four ports extending from the exterior of the second housing to the interior of the second housing to the array of detectors. Specific embodiments further comprise one or more optical elements selected from the group consisting of collimating lenses, imaging lenses, relay lenses, and filters.

Certain embodiments include an optical system comprising: (a) a plurality of bifurcated fiber optic cables, wherein each bifurcated fiber optic cable comprises a bifurcated end and a non-bifurcated end, wherein the bifurcated end comprises a first bifurcated member and a second bifurcated member; (b) a thermal cycler assembly having at least partially disposed therein the non-bifurcated end of each of the plurality of bifurcated fiber optic cables; (c) an illuminator housing having at least partially disposed therein the first bifurcated member; and (d) a detector housing having at least partially disposed disposed therein the second bifurcated member.

In particular embodiments, the illuminator housing comprises: (a) a plurality of light sources disposed within an interior of the illuminator housing; and (b) for each light source of the plurality of light sources at least one mirror disposed within the interior of the illuminator housing and configured to direct at least a portion of light emitted from each light source along a common path through at least one port extending from the interior of the illuminator housing to the exterior of the illuminator housing, wherein the first bifurcated member is at least partially disposed within the port.

In specific embodiments, the detector housing comprises: (a) a port extending from the exterior of the detector housing to the interior of the detector housing, wherein the second bifurcated member is at least partially disposed within the port; (b) a plurality of detectors disposed within the interior of the detector housing; and (c) a plurality of mirrors disposed within the interior of the detector housing and in a path of light entering the interior of the detector housing through the port extending from the exterior of the detector housing to the interior of the detector housing, wherein the plurality of mirrors are configured to direct at least a portion of light entering the interior of the detector housing through the port extending from the exterior of the detector housing to the interior of the detector housing to the plurality of detectors.

Certain embodiments comprise at least 4 bifurcated fiber optic cables. Particular embodiments comprise at least 5 light sources and at least 5 mirrors disposed within the interior of the illuminator housing. Specific embodiments comprise at least 20 detectors and at least 5 mirrors disposed within the interior of the detector housing.

The assays performed in the methods disclosed herein may be singleplex or multiplex assays. The assays performed in the methods disclosed herein may be quantitative or qualitative. In certain embodiments the assay performed using the first optical device is quantitative, and the assay performed using the second optical device is qualitative.

The term “coupled” is defined as connected, although not necessarily directly, and not necessarily mechanically. Two items are “coupleable” if they can be coupled to each other, and, when coupled, may still be characterized as “coupleable.” Unless the context explicitly requires otherwise, items that are coupleable are also decoupleable, and vice-versa. One non-limiting way in which a first structure is coupleable to a second structure is for the first structure to be configured to be coupled (or configured to be coupleable) to the second structure.

The terms “a” and “an” are defined as one or more unless this disclosure explicitly requires otherwise.

The term “substantially” and its variations (e.g., “approximately” and “about”) are defined as being largely but not necessarily wholly what is specified (and include wholly what is specified) as understood by one of ordinary skill in the art. In any disclosed embodiment, the terms “substantially,” “approximately,” and “about” may be substituted with “within [a percentage] of” what is specified, where the percentage includes 0.1, 1, 5, and 10 percent.

The terms “comprise” (and any form of comprise, such as “comprises” and “comprising”), “have” (and any form of have, such as “has” and “having”), “include” (and any form of include, such as “includes” and “including”) and “contain” (and any form of contain, such as “contains” and “containing”) are open-ended linking verbs. As a result, a method or device that “comprises,” “has,” “includes” or “contains” one or more steps or elements possesses those one or more steps or elements, but is not limited to possessing only those one or more elements. Likewise, a step of a method or an element of a device that “comprises,” “has,” “includes” or “contains” one or more features possesses those one or more features, but is not limited to possessing only those one or more features. For example, a system that comprises four channels may have more than four channels.

Furthermore, a device or structure that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any embodiment of any of the disclosed devices and methods can consist of or consist essentially of—rather than comprise/include/contain/have—any of the described elements and/or features and/or steps. Thus, in any of the claims, the term “consisting of” or “consisting essentially of” can be substituted for any of the open-ended linking verbs recited above, in order to change the scope of a given claim from what it would otherwise be using the open-ended linking verb.

Other features and associated advantages will become apparent with reference to the following detailed description of specific embodiments in connection with the accompanying drawings.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention. It is understood that for purposes of clarity, not all reference numbers are shown for every component visible in each figure.

It should be understood that the present devices and methods are not intended to be limited to the particular forms disclosed. Rather, they are to cover all modifications, equivalents, and alternatives falling within the scope of the claims.

Figure 1:
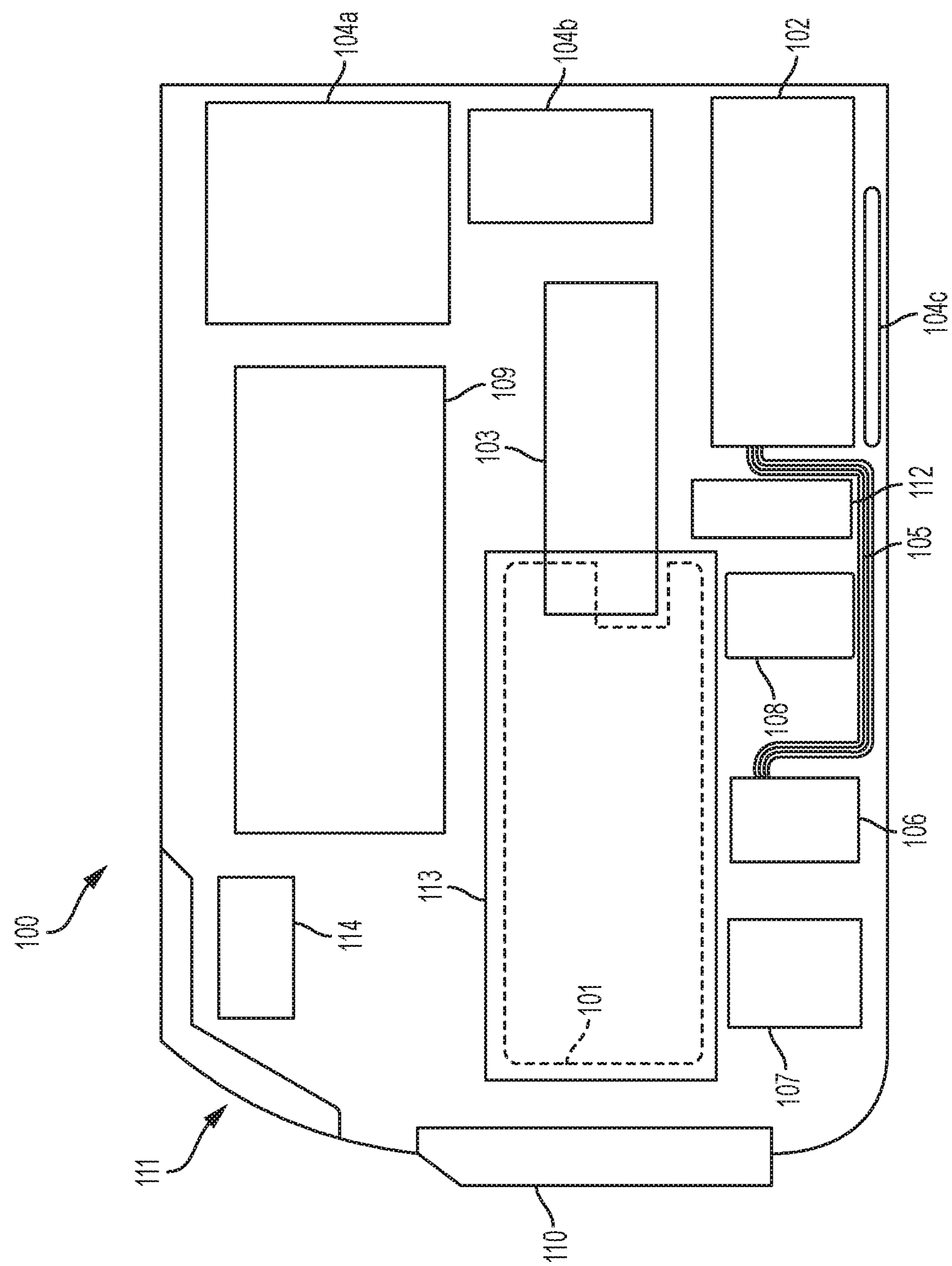
FIG. 1 is a block diagram illustrating an embodiment of a frame including a cartridge receiver, two optical devices, thermal cycler, lysis assembly, hybridization heater, and sample transfer assembly.

Referring initially to FIG. 1, which shows a cross-section view of frame 100, frame 100 is configured to receive cartridge 200 via door 110. Cartridge 200 is not shown in FIG. 1, although the dashed line 101 represents the general position that would be occupied by cartridge 200 when disposed within cartridge receiver 113 within frame 100. Frame 100 may comprise optical device 102 or optical device 103 or, as shown in FIG. 1, it may comprise both optical devices 102 and 103. In certain embodiments, frame 100 comprises a barcode reader 114 configured to scan a barcode on cartridge 200.

Optical device 102 is in optical communication with thermal cycler assembly 106 via a plurality of fiber optic cables 105. When cartridge 200 is disposed within frame 100, thermal cycler assembly 106 is configured to engage amplification tube assembly 312 of cartridge 200 such that thermal cycler assembly 106 can raise and lower the temperature of the contents of amplification tube assembly 312 according to a desired protocol. When cartridge 200 is disposed within frame 100, optical device 103 is configured to be in optical communication with hybridization imaging region 314. Lift motor 112 is configured to raise and lower optical device 103 in order to facilitate the insertion of cartridge 200 into the cartridge receiving area of frame 100 and/or facilitate the optical communication between optical device 103 and hybridization imaging region 314. Alternatively, lift motor 112 is configured to raise and lower cartridge receiver 113 in order to facilitate the insertion of cartridge 200 into the cartridge receiver 113 and/or facilitate the optical communication between optical device 103 and hybridization imaging region 314.

Lysis assembly 107 and hybridization heater 108 also are configured to engage cartridge 200 when it is disposed within frame 100. Lysis assembly 107 is configured to engage various features in the sample preparation region 401 of cartridge 200. In certain embodiments, lysis assembly 107 may comprise (i) a lysis heater configured to engage lysis well 311 and promote thermal transfer from the lysis heater to the contents of lysis well 311, (ii) a magnet configured to be selectively engaged with lysis well 311 and/or other wells of the sample preparation region 401, such that when the magnet is engaged magnetically responsive particles in cartridge 200 can be immobilized in a desired location within sample preparation region 401; and (iii) a sonication horn configured to provide acoustic energy to the contents of lysis well 311. Hybridization heater 108 is configured to engage various features in the hybridization region 403 of cartridge 200. Hybridization heater 108 comprises a heating/cooling element, such as a peltier cell or thermoelectric couple (TEC), configured to contact hybridization tube assembly 313 when cartridge 200 is disposed within frame 200. Hybridization heater 108 may further comprise (i) a heat sink to facilitate the transfer of heat away from the hybridization heater 108, (ii) one or more thermistors to profile the temperature of the hybridization heater 108, and/or (iii) a hybridization processor to facilitate electrical connection of the heating/cooling element and/or the thermistors to the frame 100 interface circuit and/or the system control circuit.

As mentioned above, thermal cycler assembly 106 is configured to engage amplification tube assembly 312 of cartridge 200 such that thermal cycler assembly 106 can raise and lower the temperature of the contents of amplification tube assembly 312 according to a desired protocol. In certain embodiments, thermal cycler assembly 106 may comprise a amplification tube block having an internal shape that fits amplification tube assembly 312 such that there is consistent contact between the inner surfaces of the amplification tube block and outer surfaces of amplification tubes 405, 406, 407, and 408. In addition, in certain embodiments, thermal cycler assembly 106 will have one or more lumens configured to receive fiber optical cables 105 such that electromagnetic radiation may be transmitted to and received from amplification tubes 405, 406, 407, and 408. Thermal cycler assembly 106 also comprises a heating/cooling element, such as a peltier cell or thermoelectric couple (TEC). Thermal cycler assembly 106 may further comprise (i) a heat sink to facilitate the transfer of heat away from the thermal cycler assembly 106, (ii) one or more thermistors to profile the temperature of the amplification tube block, and/or (iii) an amplification processor to facilitate electrical connection of the heating/cooling element and/or the thermistors to the frame 100 interface circuit and/or the system control circuit.

Sample transfer assembly 109 is configured to selectively engage pipette tips 305, 306, and 307 when cartridge 200 is disposed within frame 200. Sample transfer assembly 109 comprises one or more transfer heads which fit pipette tips 305, 306, and 307 with enough friction to prevent the pipette tips from falling off. A tip pusher is connected to the transfer head and is configured to disengage the transfer head from the pipette tip at the desired time. In embodiments in which the sample transfer assembly 109 has a single transfer head, the sample transfer assembly 109 selectively engage pipette tips 305, 306, and 307 sequentially. In embodiments in which the sample transfer assembly 109 has a multiple transfer heads, the sample transfer assembly 109 may selectively engage two or more of pipette tips 305, 306, and 307 simultaneously. The transfer head is coupled to a pressure regulating device, such as a pump, to permit fluid to be drawn into or ejected out of pipette tips 305, 306, and 307 when engaged with the transfer head. In certain embodiments, sample transfer assembly 109 comprises a device for moving the transfer head in one or more of the x, y, and z axis. For example, this may include an x-rail, a y-rail, and a z-rail, along which the transfer head travels under the power of an x-motor, a y-motor, and a z-motor.

Also shown in FIG. 1 are circuit boards 104*a*-*c*, which provide electrical connections and control circuitry to the various components of frame 100.

Figure 3:
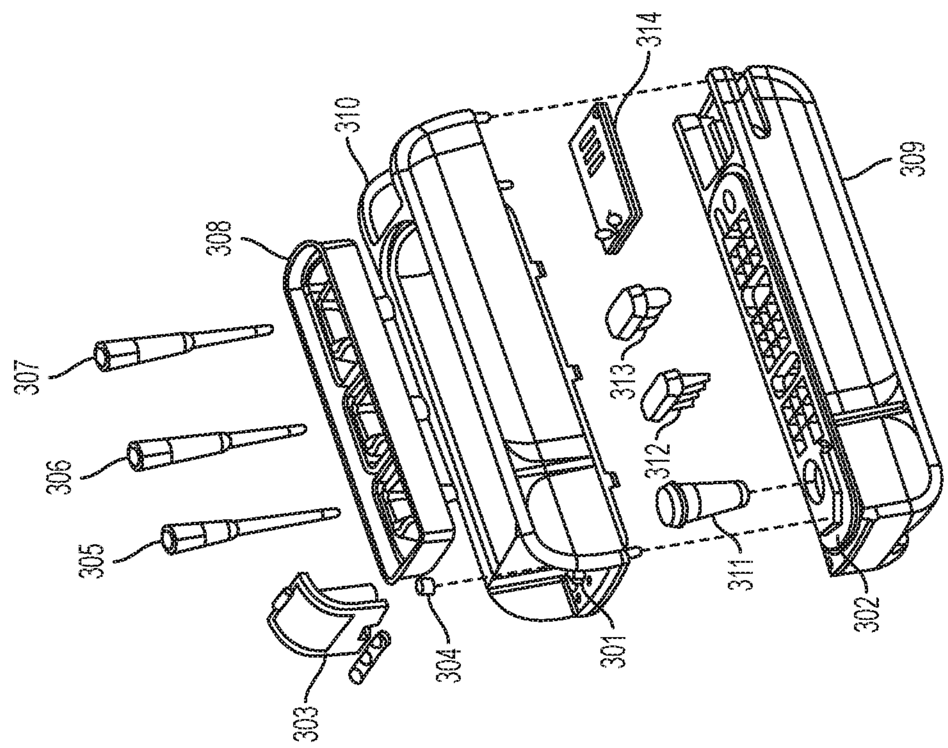
FIG. 3 is a drawing showing an exploded view of one embodiment of a cartridge.
Figure 2:
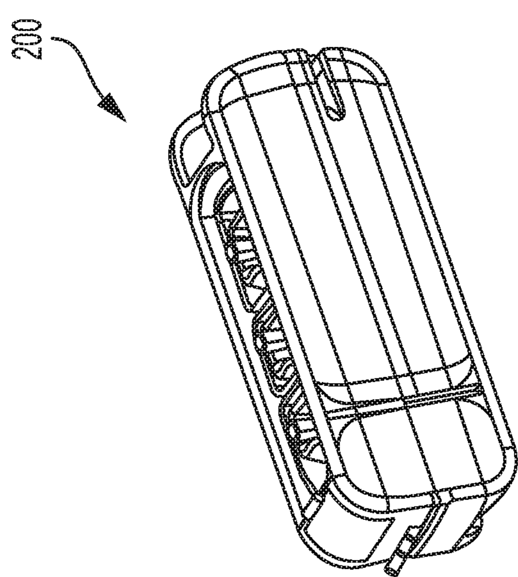
FIG. 2 is a drawing showing a perspective view of one embodiment of a cartridge.

FIG. 2 shows a perspective view of cartridge 200 and FIG. 3 shows an exploded view of cartridge 200. As shown in FIG. 3, cartridge 200 comprises a reagent tray 309 in which are located a number of structural features including sample well 302, lysis well 311, amplification tube assembly 312, hybridization tube assembly 313, and various additional reagent wells.

Figure 4A:
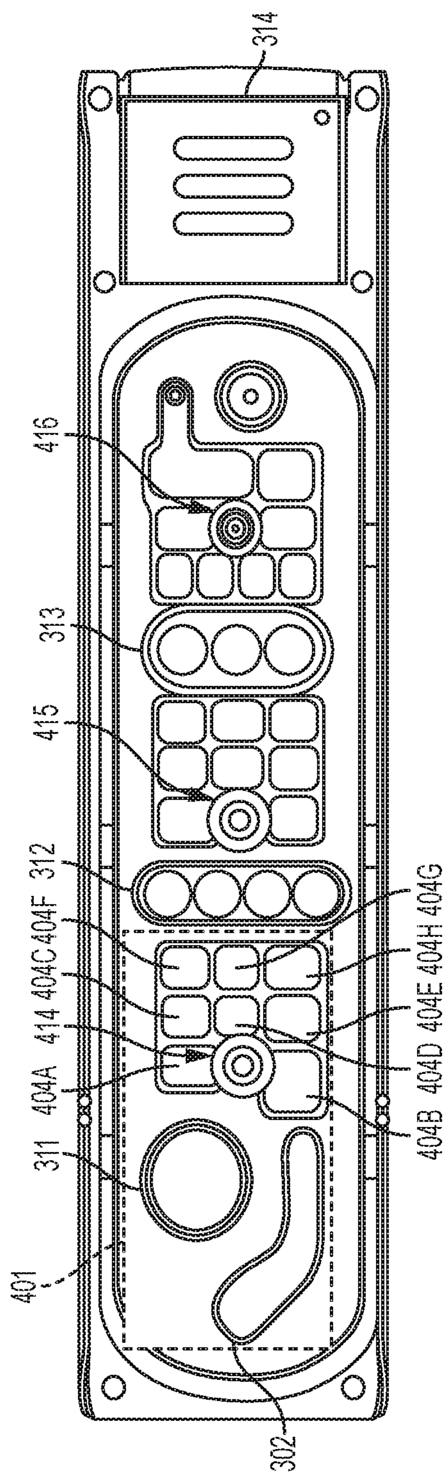
FIGS. 4A-4C are drawings showing a cut-away top view of one embodiment of a cartridge.
Figure 4B:
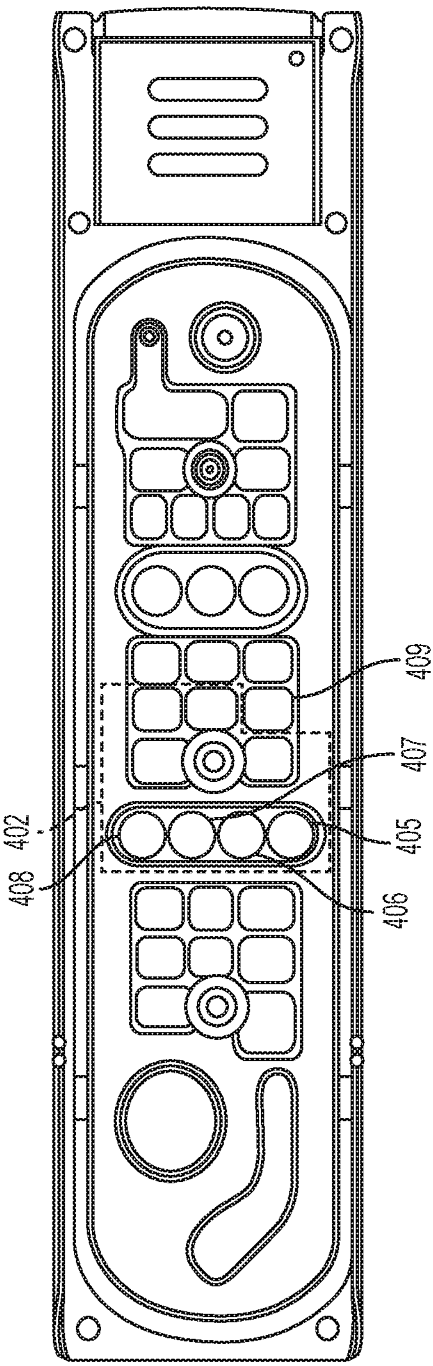
Figure 4C:
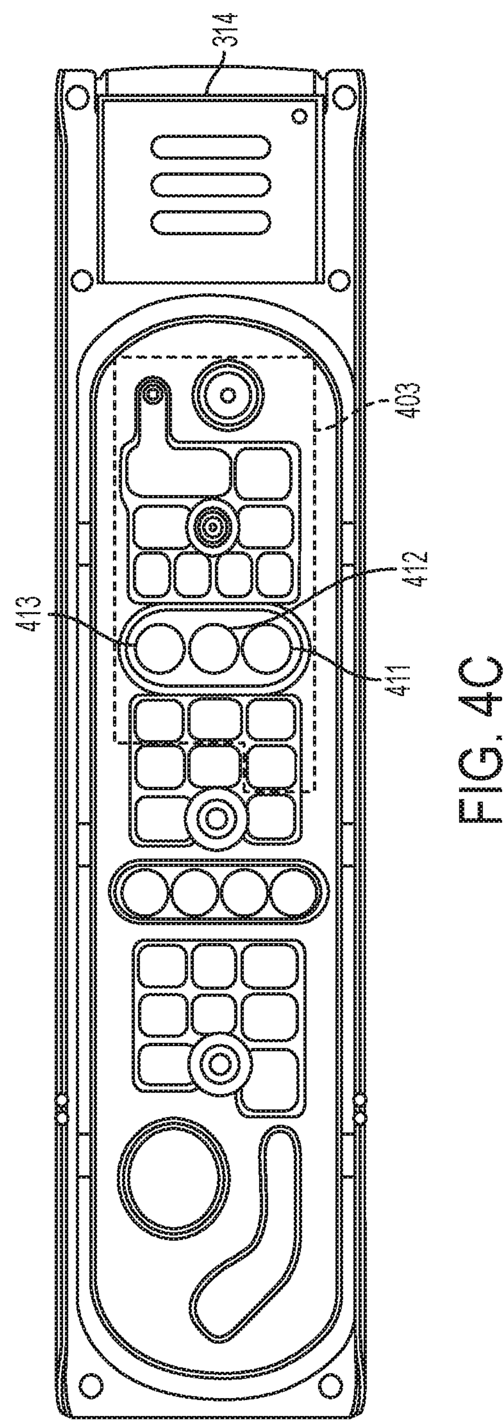

FIGS. 4A-4C are drawings showing a cut-away top view of one embodiment of a cartridge. In this embodiment, the cartridge has three pipette tips, which may be disposed with pipette storage cavities 414, 415, and 416, respectively, when not in use. Pipette storage cavity 414 and the sample prep pipette are located within sample preparation region 401 indicated by the dashed line in FIG. 4A. Sample preparation region 401 also includes a sample well 302 and a lysis well 311. In addition, sample preparation region 401 may include one or more additional wells, such as those indicated by 404A-H, which may contain sample preparation reagents (e.g., lysis buffers, magnetic particles), be used for mixing or transferring the sample and reagents, or be used for holding waste. The sample prep pipette is movable in the x, y, and z axes, such that it can access each well in sample preparation region 401. The sample prep pipette may also access the tubes of PCR tube assembly 312 in order to transfer the sample from sample preparation region 401 to amplification region 402.

Pipette storage cavity 415 and the amplification pipette are located within amplification region 402 indicated by the dashed line in FIG. 4B. Amplification region 402 also includes PCR tubes 405, 406, 407, and 408. In addition, amplification region 402 may include additional wells for holding or mixing amplification reagents. The amplification pipette is movable in the x, y, and z axes, such that it can access each well in amplification region 402. The amplification pipette may also access certain wells of sample preparation region 410 and/or hybridization region 403 in order to transfer the sample between regions.

Pipette storage cavity 416 and the hybridization pipette are located within hybridization region 403 indicated by the dashed line in FIG. 4C. The hybridization region 403 also includes hybridization wells 411, 412, and 413, as well as an opening for transferring the sample to hybridization imaging region 314. In addition, hybridization region 403 may include one or more additional wells, which may contain hybridization reagents (e.g., hybridization buffers, probes), be used for mixing or transferring the sample and reagents, or be used for holding waste. The hybridization pipette is movable in the x, y, and z axes, such that it can access each well in hybridization region 403. The hybridization pipette may also access certain wells in amplification region 402 in order to transfer the sample amplification region 402 to hybridization region 403.

Figure 5A:
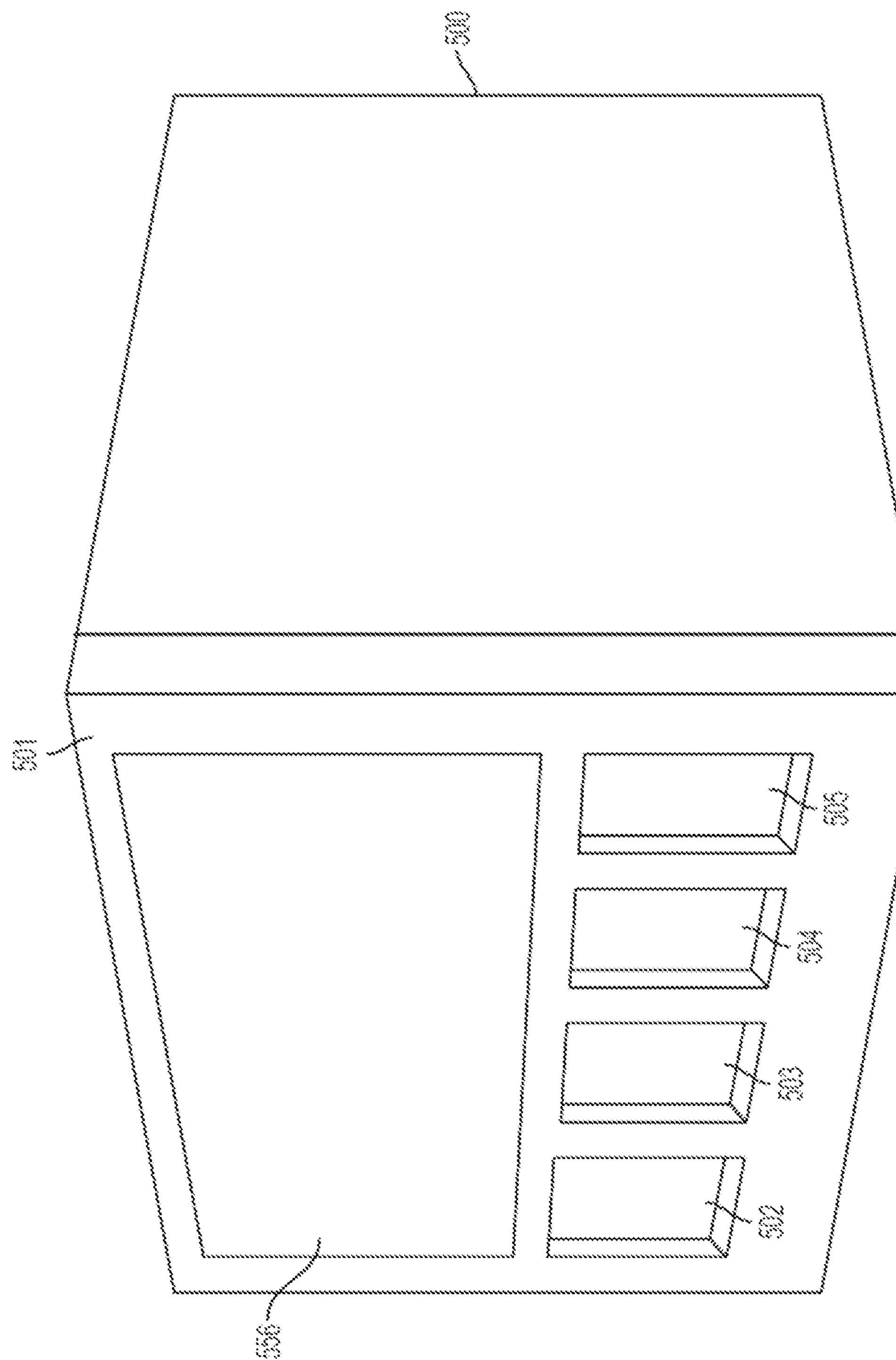
FIG. 5A is a drawing showing a perspective view of one embodiment of a housing with its door closed.
Figure 5B:
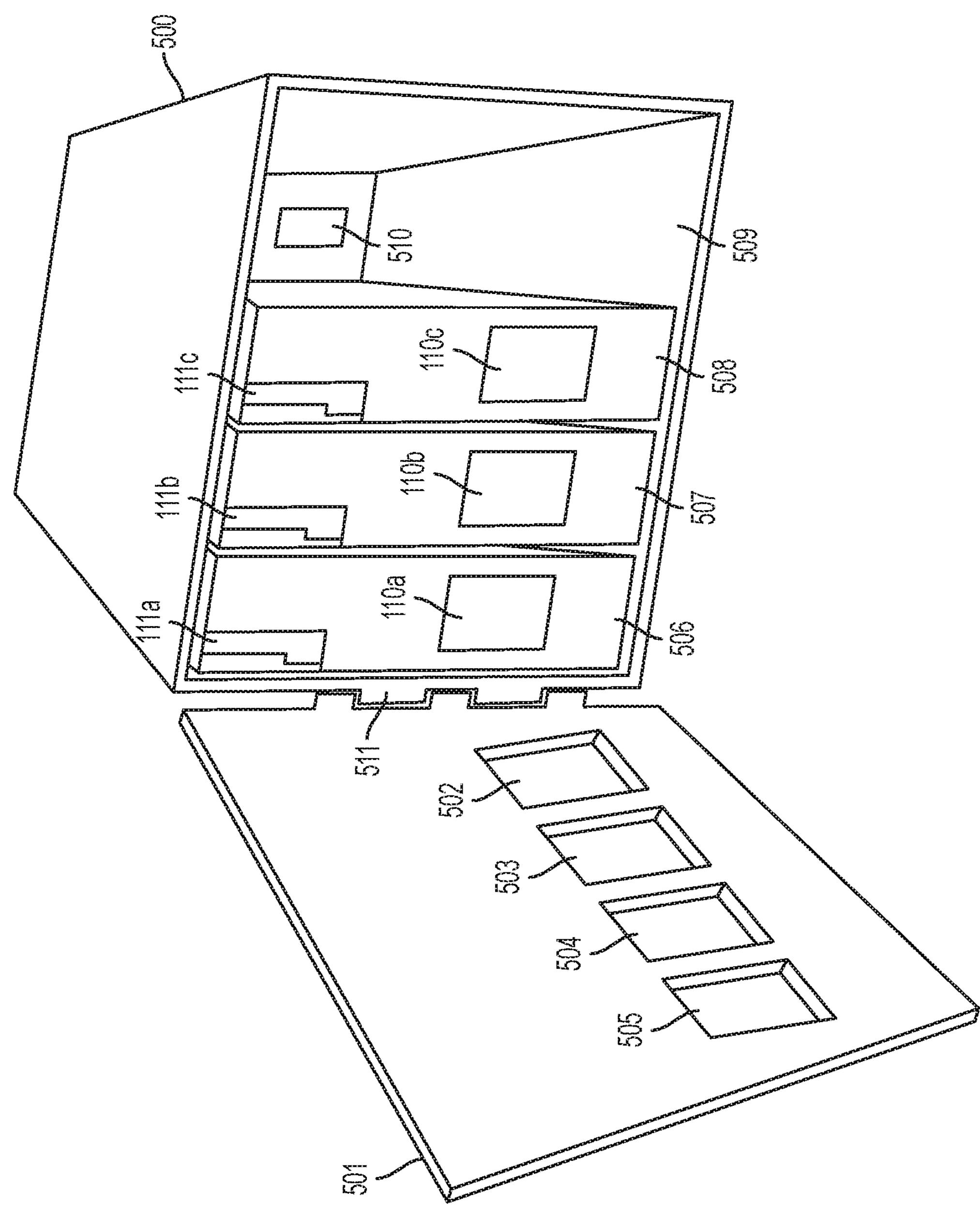
FIG. 5B is a drawing showing a perspective view of one embodiment of a housing with its door open.

Referring now to FIGS. 5A and 5B, one or more frames 100 can be disposed within a housing 500. A housing can be configured to accommodate any number of frames, such as 1, 2, 3, 4, 5, 6, 7, 8, 9, 10, 11, or 12 frames. The embodiment shown in FIGS. 5A and 5B is configured to accommodate 4 frames. Housing 500 includes a door 501. Door 501 includes a touchscreen user interface 556 and openings 502, 503, 504, and 504 through which a cartridge could be inserted into the frames 100 inside housing 500. Door 501 is mounted on hinge 511 such that it can be swung open permitting access to the interior of housing 500 as shown in FIG. 5B. FIG. 5B shows 3 frames, 506, 507, and 508 within housing 500. Empty bay 509 and electrical connection 510 are unused, but provide the option of expanding the capacity and/or functionality of the system by adding a fourth frame. Frames 506, 507, and 508 each include a door (110*a*, 110*b*, and 110*c*) through which a cartridge can be inserted into or removed from the frame, and a housing engagement (111*a*, 111*b*, and 111*c*) for engaging and disengaging the frame with housing 500.

An optical device, such as optical device 102 shown in FIG. 1, may include an illuminator and a detector. The illuminator comprises one or more optical elements such as, for example, LEDs, filters, dichroic mirrors, broadband mirrors, aspherical collimators, and/or spherical relay lenses. The detector comprises one or more optical elements such as, for example, filters, dichroic mirrors, broadband mirrors, aspherical collimators, spherical condensers, charge couple devices, photodiodes, and/or photomultipliers.

Figure 6:
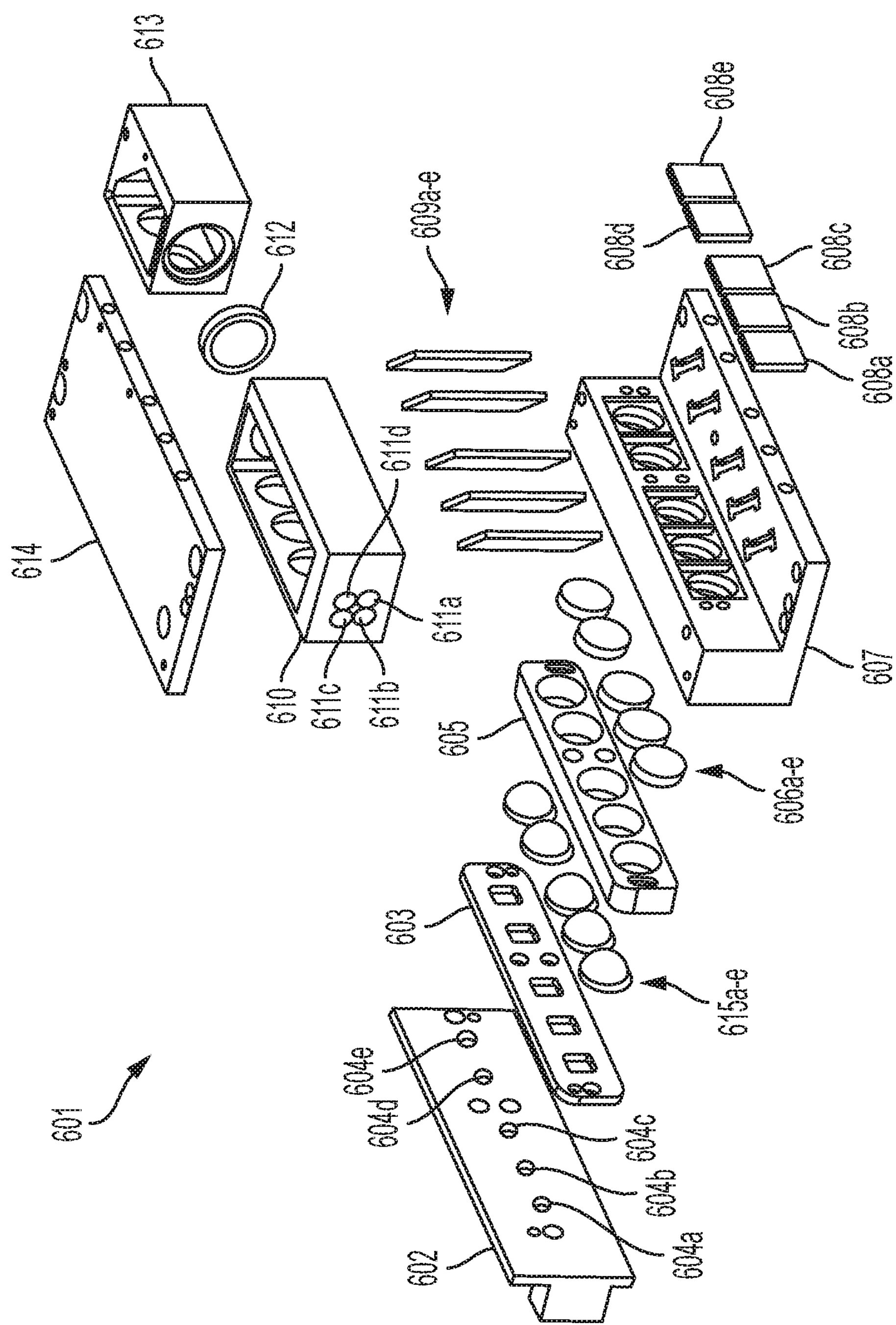
FIG. 6 is a drawing showing an exploded view of one embodiment of an illuminator.
Figure 7:
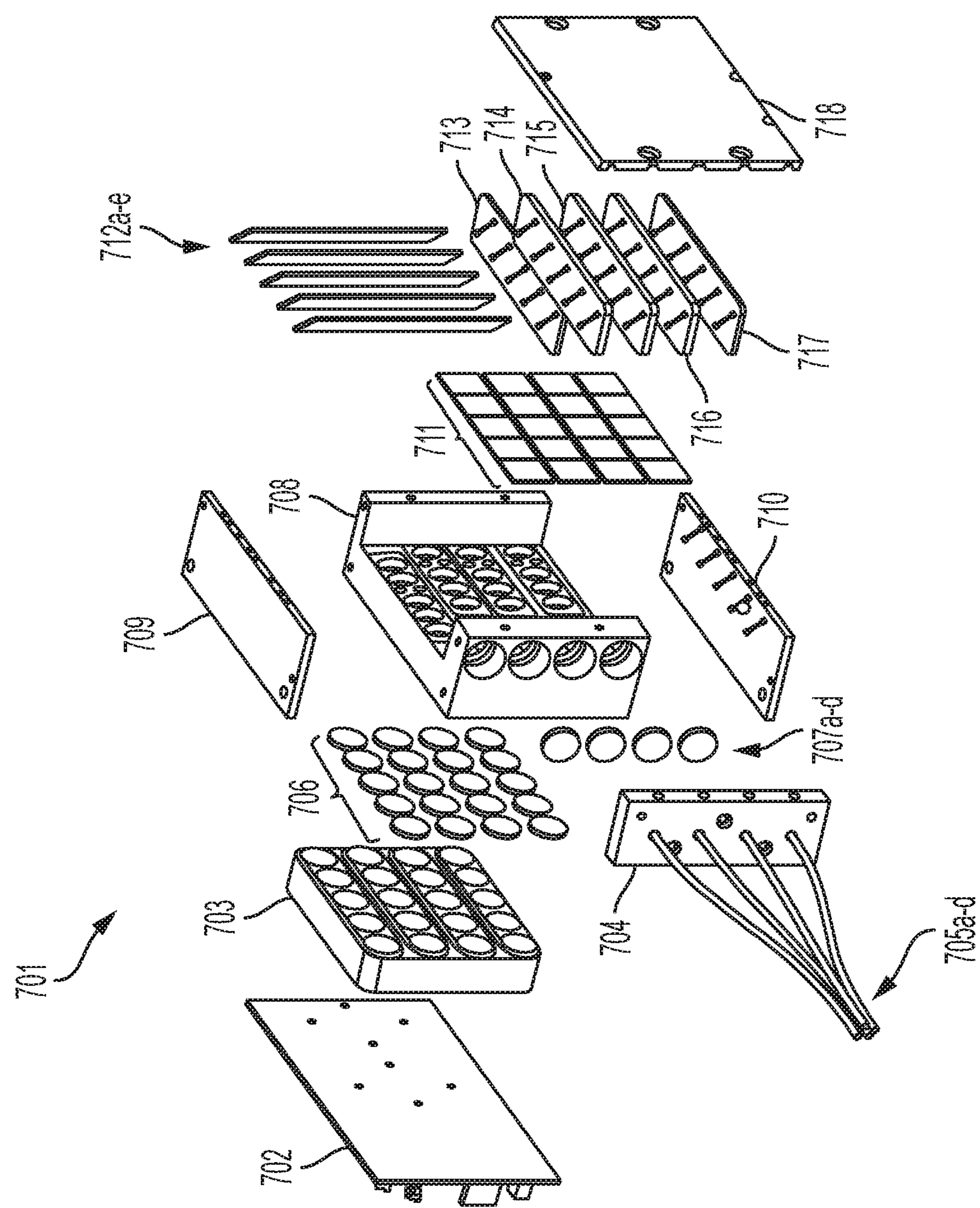
FIG. 7 is a drawing showing an exploded view of one embodiment of a detector.

In certain embodiments, the optical device includes an illuminator, such as illuminator 601 shown in an exploded view in FIG. 6, and a detector, such as detector 701 shown in an exploded view in FIG. 7. Turning to FIG. 6, the illuminator illustrated in this embodiment comprises a collection of five light emitting diodes (LEDs) 604*a-e*, which are mounted on LED board 602. Light emitted from each of LEDs 604*a-e* is transmitted through a corresponding collimating lens in the collection of collimating lenses 615*a-e*, then to a corresponding imaging lens 606*a-e*, and then to a corresponding spectral filter in the collection of spectral filters 608*a-e*. Each filter in the collection of excitation filters 608*a-e* is unique in that each filter is configured to transmit a wavelength or range of wavelengths of light that is different from the other filters in the collection of excitation filters 606*a-e*. A lens spacer 603 is disposed between LED board 602 and collimating lenses 615*a-e*. Lens spacer 605 is disposed between collimating lenses 615*a-e* and imaging lens 606*a-e*.

After passing through the collection of excitation filters 608*a-e*, the light is transmitted to a collection of mirrors 609*a-e*. In certain embodiments, each mirror in the collection of mirrors 609*a-e* is a dichroic mirror. In some embodiments, however, mirror 609*e* may be a broadband mirror. Excitation filters 608*a-e* and mirrors 609*a-e* are mounted on base plate 607. Light reflected from mirrors 609*a-e* is directed toward fiber optic cables, which will direct the light to the PCR tubes of a cartridge. In the embodiment in FIG. 6, there are four ports 611*a-d* in front illuminator housing 610, and each port is configured to have one fiber optical cable disposed therein. Front illuminator housing 610 is enclosed on one side by cover 614. Light wavelengths emitted from each of the LEDs 604*a*-3 and transmitted by the other optical elements of illuminator 601 are combined and transmitted through each of the four fiber optic cables disposed in ports 611*a-d* in front illuminator housing 610. Disposed between dichroic mirrors 609*c* and 609*d* is relay lens 612. Relay lens 612 focuses the wavelengths of light reflected by mirrors 609*d* and 609*e* which are located in back illuminator housing 613, in the direction of the fiber optic cables disposed in ports 611*a-d*. The other end of each of the fiber optic cables is disposed within a lumen in the thermal cycler assembly such that light from the illuminator can be transmitted to the thermal cycler assembly and the amplification tubes that may be disposed therein.

Turning to FIG. 7, the detector illustrated in this embodiment comprises four collimating lenses 707*a-d*, each of receives light from a corresponding one of fiber optic cables 705*a-d*. From collimating lenses 707*a-d*, light is transmitted to mirrors 712*a-e*. In certain embodiments, each mirror in the collection of mirrors 712*a-e* is a dichroic mirror. In some embodiments, however, mirror 712*e* may be a broadband mirror. Mirrors 712*a-e* are disposed within a housing comprising frame 708, cover 718, and end caps 709 and 710. Channel isolators 713, 714, 715, 716, and 717 assist in keeping the light path from each fiber optic cable isolated. Light reflected by mirrors 712*a-e* passes through a corresponding emission filter in the collection of emission filters 711. As can be seen in FIG. 7, there are five emission filters for each of the four fiber optic cables 705*a-d*. Accordingly, the collection of emission filters 711 contains 20 emission filters. Each set of five emission filters receiving light from one of the fiber optic cables is unique in that each filter is configured to transmit a wavelength or range of wavelengths of light that is different from the other filters in that set. Wavelengths passing through each of the emission filters of the collection of emission filters 711 is transmitted through a corresponding focusing lens in the collection of focusing lenses 706 and on to photodiode detector board 702, which comprises 20 photodiode detectors. Focusing lenses 706 are mounted to lens block 703.

In certain embodiments, a bifurcated fiber optic cable is used to place the optical device in optical communication with the thermal cycler assembly. In such an embodiment, the bifurcated end of the fiber optic cable is disposed in the optical device with one of the bifurcated ends being disposed in the illuminator and the other bifurcated end being disposed in the detector. Also in such an embodiment, the non-bifurcated end may be disposed in the thermal cycler assembly. The excitation wavelength(s) of electromagnetic radiation is transmitted from the illuminator to the contents of PCR tube in the thermal cycler assembly via the bifurcated fiber optic cable, and the emission wavelength(s) of electromagnetic radiation is transmitted from the contents of the PCR tube in the thermal cycler assembly to the detector via the bifurcated fiber optic cable.

The above specification and examples provide a complete description of the structure and use of an exemplary embodiment. Although certain embodiments have been described above with a certain degree of particularity, or with reference to one or more individual embodiments, those skilled in the art could make numerous alterations to the disclosed embodiments without departing from the scope of this invention. As such, the illustrative embodiment of the present devices is not intended to be limited to the particular forms disclosed. Rather, they include all modifications and alternatives falling within the scope of the claims, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

REFERENCES

The following references are incorporated herein by reference:

U.S. Pat. Pub. 2014/0005078
U.S. Pat. Pub. 2014/0038192
U.S. Pat. Pub. 2015/0308958
U.S. Pat. No. 9,827,567
U.S. Pat. No. 9,248,422
U.S. Pat. No. 7,695,952
U.S. Pat. No. 7,773,790
U.S. Pat. No. 7,888,107
U.S. Pat. No. 7,396,677
U.S. Pat. No. 6,750,016
U.S. Pat. No. 6,602,669
U.S. Pat. No. 6,506,564
U.S. Pat. No. 7,321,829
U.S. Pat. No. 7,250,499
U.S. Pat. No. 5,538,848
U.S. Pat. No. 5,804,375
U.S. Pat. No. 7,422,850
U.S. Pat. No. 8,698,101
U.S. Pat. No. 9,115,393

We claim:

1. An apparatus, comprising:

an instrument housing comprising a plurality of instrument bays, each of which is configured to hold a corresponding biological assay frame;

a biological assay control circuit configured to:

receive, via a user interface, a request to perform a biological assay on at least one sample inserted into a particular biological assay frame within the instrument housing; and instruct the particular biological assay frame to perform the request to perform the biological assay; and output, via the user interface based on information received from the biological assay frame, results of the biological assay;

a plurality of electrical connectors configured to connect the biological assay control circuit to biological assay frames held within each of the plurality of instrument bays a first biological assay frame disposed within a first instrument bay of the plurality of instrument bays;

a second biological assay frame disposed within a second instrument bay of the plurality of instrument bays; and a third biological assay frame disposed within a third instrument bay of the plurality of instrument bays.

2. The apparatus of claim 1, wherein at least one of the first, second, and third biological assay frames comprises:

an enclosure configured to receive a cartridge that includes a biological sample;

a first optical device configured to perform a first optical assay on a first region of the cartridge when the cartridge is disposed in the enclosure;

a second optical device configured to perform a second optical assay on a second region of the cartridge when the cartridge is disposed in the enclosure, wherein the second optical assay is a different type of optical assay than the first optical assay; and an interface circuit configured to receive electronic instructions to use the first optical device to perform the first optical assay on a first subset of the biological sample, and to use the second optical device to perform a second optical assay on a second subset of the biological sample.

3. The apparatus of claim 2, wherein the at least one of the first, second, and third biological assay frames comprises: the enclosure configured to receive the cartridge that includes a biological sample; the second optical device configured to perform the second optical assay on the second region of the cartridge when the cartridge is disposed in the enclosure; and an interface circuit configured to receive electronic instructions to use the second optical device to perform an optical assay on the biological sample in the second region of the cartridge; wherein the at least one of the first, second, and third biological assay frames does not have the first optical device configured to perform the first optical assay on the first region of the cartridge when the cartridge is disposed in the enclosure.

4. A method for performing a multiplex biological assay comprising:

inserting a cartridge that includes a biological sample into an apparatus according to claim 2;

using the first optical device to perform a first optical assay on the biological sample in the first region of the cartridge; and using the second optical device to perform a second optical assay on the biological sample, wherein the second optical assay is different from the first optical assay.

5. The method of claim 4, wherein: the first optical assay is a real time polymerase chain reaction performed on a first subset of a plurality of target nucleic acid sequences in the biological sample; and the second optical assay is an end-point analysis of a polymerase chain reaction performed on a second subset of the plurality of target nucleic acid sequences in the biological sample.

6. The method of claim 5, wherein the first subset of the target nucleic acid sequences comprises from one to six target nucleic acid sequences.

7. The method of claim 5, wherein the second subset of the target nucleic acid sequences comprises from one to thirty target nucleic acid sequences.

8. The method of claim 5, further comprising quantitating the amount of target nucleic acid sequences in the first subset of the target nucleic acid sequences.

9. A method for performing a multiplex biological assay comprising:

inserting a cartridge that includes a biological sample comprising proteins and nucleic acids into an apparatus according to claim 2;

transferring a first subset of the biological sample from a sample well of the cartridge to the first region of the cartridge;

transferring a second subset of the biological sample from the sample well of the cartridge to the second region of the cartridge;

using the first optical device to detect a polymerase chain reaction performed on the first subset of the biological sample in the first region of the cartridge; and using the second optical device to detect an immunoassay performed on the second subset of the biological sample in the second region of the cartridge.

10. The apparatus of claim 2, wherein the first optical device comprises:

a fluorimeter; and a plurality of optical cables configured to transmit light between the fluorimeter and the first region of the cartridge when the cartridge is disposed in the enclosure.

11. The apparatus of claim 2, wherein the second optical device comprises:

a light source configured to illuminate the second region when the cartridge is disposed in the enclosure; and a detector configured to receive a light that is scattered or emitted from the second region when the cartridge is disposed in the enclosure.

12. The apparatus of claim 2, further comprising a thermal cycler configured to receive the first region of the cartridge.

13. The apparatus of claim 12, wherein the thermal cycler has one or more openings configured to receive one or more optical cables.

14. The method of claim 4 wherein:

the first optical assay is an optical analysis of a real-time PCR assay; and the second optical assay is an optical analysis of a nucleic acid hybridization array assay.

15. The method of claim 14 wherein the nucleic acid hybridization array assay comprises immobilized microspheres.

16. The method of claim 15, wherein the immobilized microspheres are fluorescently encoded microspheres immobilized on a surface of the second region.

17. The method of claim 16, wherein (i) the fluorescently encoded microspheres are magnetically responsive, (ii) the apparatus further comprises a magnet configured to produce a magnetic field in the second region of the cartridge when the cartridge is disposed in the enclosure, and (iii) the magnetic field immobilizes the fluorescently encoded microspheres on the surface of the second imaging region.

* * * * *